United States Patent [19]

Köppe et al.

[11] Patent Number: 4,609,672
[45] Date of Patent: * Sep. 2, 1986

[54] 1-(ALKANOYLAMINO-ARYLOXY)-2-HYDROXY-3-(ALKINYL-AMINO)-PROPANES AND SALTS THEREOF

[75] Inventors: Herbert Köppe; Werner Kummer; Helmut Stähle; Gojko Muacevic, all of Ingelheim am Rhein; Werner Traunecker, Münster-Sarmsheim, all of Fed. Rep. of Germany

[73] Assignee: C. H. Boehringer Sohn, Ingelheim am Rhein, Fed. Rep. of Germany

[*] Notice: The portion of the term of this patent subsequent to Aug. 17, 1999 has been disclaimed.

[21] Appl. No.: 623,960

[22] Filed: Jun. 25, 1984

Related U.S. Application Data

[63] Continuation of Ser. No. 241,471, Mar. 9, 1981, abandoned.

[30] Foreign Application Priority Data

Mar. 8, 1980 [DE] Fed. Rep. of Germany ....... 3009047

[51] Int. Cl.$^4$ ........................................... A61K 31/275
[52] U.S. Cl. ...................................... 514/522; 558/414
[58] Field of Search ................. 514/522; 260/465 D

[56] References Cited

U.S. PATENT DOCUMENTS 3,925,446 12/1975 Koppe et al. ................. 424/304
4,344,964 8/1982 Koppe et al. ................. 424/304

Primary Examiner—Frederick E. Waddell
Attorney, Agent, or Firm—Hammond & Littell, Weissenberger & Dippert

[57] ABSTRACT

The invention relates to a compound of the formula

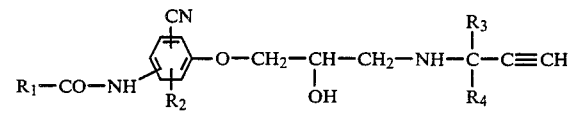

wherein $R_1$ is a linear or branched alkyl of 4 to 20 carbon atoms;
$R_2$ is hydrogen, halogen, alkyl of 1 to 4 carbon atoms, alkoxy of 1 to 4 carbon atoms or a bivalent radical —CH=CH—CH=CH— or —$(CH_2)_n$—, where n is an integer from 3 to 5, inclusive, and the free bonds of said bivalent radical are attached to adjacent carbon atoms of the phenyl ring; and
$R_3$ is hydrogen or alkyl of 1 to 3 carbon atoms;
$R_4$ is alkyl of 1 to 3 carbon atoms; or
$R_3$ and $R_4$, together with each other, are —$(CH_2)_p$—, where p is an integer from 4 to 6, inclusive, or a non-toxic, pharmacologically acceptable acid addition salt thereof. The compounds of formula I are useful for treatment and prophylaxis of diseases of the coronaries, for the treatment of hypertension, and for treatment of cardiac arrhythmia, particularly tachycardia.

26 Claims, No Drawings

1-(ALKANOYLAMINO-ARYLOXY)-2-HYDROXY-3-(ALKINYL-AMINO)-PROPANES AND SALTS THEREOF

This application is a continuation of co-pending U.S. patent application Ser. No. 241,471, filed Mar. 9, 1981, now abandoned.

This invention relates to novel 1-(alkanoylaminoaryloxy)-2-hydroxy-3-(alkinyl-amino)-propanes and non-toxic acid addition salts thereof, to methods of preparing these compounds, to pharmaceutical compositions containing them as active ingredients, and to methods of using them for the treatment of tachycardia, hypertension and disorders of the coronary vessels.

More particularly, the present invention relates to a novel class of compounds represented by the formula

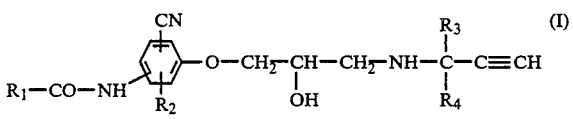

wherein
- $R_1$ is a linear or branched alkyl of 4 to 20 carbon atoms;
- $R_2$ is hydrogen, halogen, alkyl of 1 to 4 carbon atoms, alkoxy of 1 to 4 carbon atoms, or a bivalent radical —CH=CH—CH=CH— or —(CH$_2$)$_n$—, where n is an integer from 3 to 5, inclusive, and the free bonds of said bivalent radical are attached to adjacent carbon atoms of the phenyl ring; and
- $R_3$ is hydrogen or alkyl of 1 to 3 carbon atoms;
- $R_4$ is alkyl of 1 to 3 carbon atoms; or
- $R_3$ and $R_4$, together with each other, are —(CH$_2$)$_p$—, where p is an integer from 4 to 6, inclusive, and non-toxic, pharmacologically acceptable acid addition salts thereof.

The compounds embraced by formula I may be prepared by the following methods:

Method A

By reacting a compound of the formula

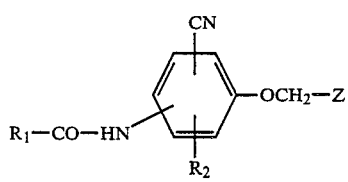

wherein
$R_1$ and $R_2$ have the same meanings as in formula I, and
Z is

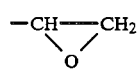

or —CH(OH)—CH$_2$—Hal, where Hal is halogen, with an amine of the formula

wherein $R_3$ and $R_4$ have the same meanings as in formula I.

Method B

By hydrolyzing an oxazolidine derivative of the formula

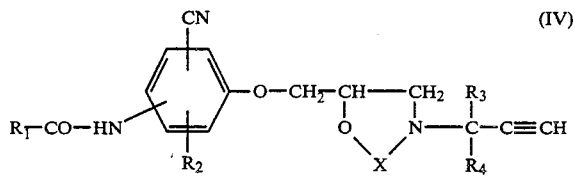

wherein
$R_1$, $R_2$, $R_3$ and $R_4$ have the same meanings as in formula I, and
X is —CO—, —CH$_2$— or —CH(lower alkyl)—,
with an aqueous solution of sodium hydroxide or potassium hydroxide, or with a mixture of ethanol and water.

Method C

By reacting a compound of the formula

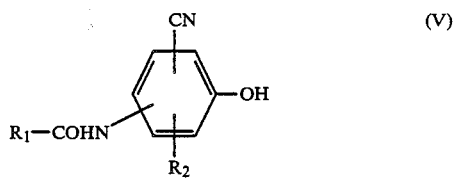

wherein $R_1$ and $R_2$ have the same meanings as in formula I, or a salt thereof, with an azetidinol derivative of the formula

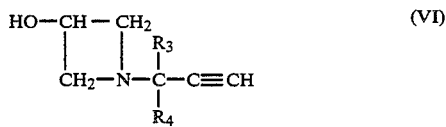

wherein $R_3$ and $R_4$ have the same meanings as in formula I, in an anhydrous medium.

The oxazolidinone starting compounds of the formula IV, i.e., those where X is —CO—, may be prepared by reacting an epoxide of the formula II with a urethane of the formula

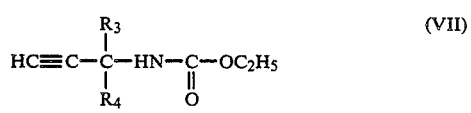

wherein $R_3$ and $R_4$ have the same meanings as in formula I. A urethane of the formula VII is obtained by reacting ethyl chloroformate with an amine of the formula III.

The starting comounds of the formula V are known compounds and may be prepared by methods which are described in the literate. The starting compounds of the formula VI may be prepared, for example, by the method described in Chem. Pharm. Bull. (Japan), Vol. 22(7), 1974, page 1490.

The compounds of the formula I comprise an asymmetric carbon atom in the —CH(OH)— group and therefore occur as racemates and as optical antipodes. The latter may be isolated not only by separation of the racemate with the aid of conventional auxiliary acids, such as dibenzoyl-D-tartaric acid, di-p-toluyl-D-tartaric acid, or D-3-bromocamphor-8-sulfonic acid, but also by using the corresponding optically active starting material.

The compounds of the formula I are basic and therefore form addition salts with inorganic or organic acids. Examples of non-toxic, pharmacologically acceptable acid addition salts are those formed with hydrochloric acid, hydrobromic acid, sulfuric acid, methane-sulfonic acid, maleic acid, acetic acid, oxalic acid, lactic acid, tartaric acid, 8-chlorotheophylline, or the like.

The following examples illustrate the present invention and will enable others skilled in the art to understand it more completely. It should be understood, however, that the invention is not limited solely to the particular examples given below.

EXAMPLE 1

1-(2-Cyano-4-α-methylpentanoylamino-phenoxy)-3-(2-methylbutinyl-3-amino-2)-2-propanol Fourteen grams (0.048 mol) of 1-(2-cyano-4-α-methylpentanoylamino-phenoxy)-2,3-epoxypropane were dissolved in 100 ml of ethanol. After addition of 12.5 gm (0.15 mol) of 2-methylbutine-3-amine-2, the mixture was refluxed for one hour. After cooling, the solvent was distilled off in vacuo, and the residue was stirred with dilute HCl and extracted twice with ether. The aqueous phase was adjusted alkaline with $NH_4OH$, and the precipitating oily base was taken up in ethyl acetate. The organic phase was washed with water, dried over $MgSO_4$, and filtered. The solvent was distilled off, and the residue was purified over a silica gel column [ethyl acetate/isopropanol/$NH_4OH$ (7:3:1)]. The fractions of the pure substance yielded, after distillation, 7.6 gm of base, and the latter was taken up in ether and washed with water. After drying over $MgSO_4$ and active charcoal, the product was subjected to suction filtration and the ether was distilled off. There remained a non-crystallizing, viscous base. DC uniform. Yield: 7.4 gm.

EXAMPLE 2

1-(2-Cyano-4-n-hexanoylamino-phenoxy)-3-(2-methylbutinyl-3-amino-2)-2-propanol

An amount of 41.3 gm (0.18 mol) of 1-(2-cyano-4-n-hexanoylamino-phenoxy)-2,3-epoxypropane was dissolved in 400 ml of ethanol and, after addition of 33.2 gm (0.4 mol) of 2-methylbutin-3-amine-2, the mixture was refluxed for 1.5 hours. After the solvent was distilled off, the dark residue was recrystallized from 250 ml of acetonitrile. The raw crystals were subjected to suction filtration and then recrystallized once more from 250 ml of acetonitrile with addition of active charcoal. An amount of 16.9 gm of pure white crystals was obtained. M.p.: 119°–122° C.

EXAMPLE 3

1-(2-Cyano-4-α-ethylbutyroylamino-phenoxy)-3-(2-methylbutinyl-3-amino-2)-2-propanol hydrochloride Fourteen grams (0.049 mol) of 1-(2-cyano-4-α-ethylbutyroylamino-phenoxy)-2,3-epoxypropane were dissolved in 100 ml of ethanol, and, after addition of 12.5 gm (0.15 mol) of 2-methylbutin-3-amine-2, the mixture was refluxed for one hour. The solvent was distilled off i.v., and the remaining residue was purified over a silica gel column as described in Example 1. The pure product thus obtained was dissolved in 50 ml of acetonitrile, ethanolic HCl was added, and the hydrochloride was brought to crystallization by addition of ether. After isolation and drying, 4.5 gm of pure white crystals were obtained. M.p.: 202°–205° C.

EXAMPLE 4

1-[2-Cyano-4-(3,3-dimethylbutyroylamino)-phenoxy]-3-(2-methylbutinyl-3-amino-2)-2-propanol hydrochloride Fourteen grams (0.049 mol) of 1-[2-cyano-4-(3,3-dimethylbutyroylamino)-phenoxy]-2,3-epoxypropane were dissolved in 100 ml of ethanol and, after addition of 12.5 gm (0.15 mol) of 2-methylbutin-3-amine-2, the mixture was refluxed for one hour, as described in Example 3. After the solvent was distilled off, the residue was treated with dilute HCl, whereby the greater part dissolved. For the separation of non-basic portions, the ether was extracted and the aqueous phase was adjusted alkaline with $NH_4OH$. The separating base was taken up with ethyl acetate. This was washed with water and dried over $MgSO_4$, and the solvent was removed by distillation.

The residue was purified over a silica gel column as described in Example 1. After the fraction was processed, there remained a viscous residue which was dissolved in ethanol and stirred with ethanolic HCl. The solvent was distilled off i.v., the residue was dissolved in a small amount of acetonitrile, and alcoholic HCl was added. After addition of ether, the hydrochloride precipitated in crystalline form. An amount of 5.8 gm of pure white crystals was obtained. M.p.: 186°–188° C.

EXAMPLE 5

1-(2-Cyano-4-n-octanoyl-aminophenoxy)-3-(2-methylbutinyl-3-amino-2)-propanol

Ten grams (0.03 mol) of 1-(2-cyano-4-n-octanoylaminophenoxy)-2,3-epoxypropane were dissolved in 80 ml of ethanol and, after addition of 10 ml of 2-methylbutin-3-amine-2, the mixture was refluxed for 80 minutes. The refluxed mixture was permitted to cool, the solvent was distilled off, and the crystalline residue was recrystallized from acetonitrile. The pure white crystals were then recrystallized again from acetonitrile, whereby 3.7 gm of pure base was obtained. M.p.: 110°–112° C.

EXAMPLE 6

1-(2-Cyano-4-n-hexanoylaminophenoxy)-3-(1-ethinyl-cyclohexylamino)-propanol-2

An amount of 10.4 gm (0.033 mol) of 1-(2-cyano-4-n-hexanoylaminophenoxy)-3-chloro-propanol-2 was refluxed in 80 ml of ethanol with 12.3 gm (0.1 mol) of 1-ethinylcyclohexylamine for 3.5 hours. After evaporation i.v. of the solvent, the residue was treated with dilute HCl and extracted with ether twice, and then the separated oily product and the aqueous phase were admixed with $NH_4OH$ and extracted with ethyl acetate.

The organic phase was washed with water, dried over $MgSO_4$, and evaporated to dryness i.v. The solid residue was recrystallized twice from acetonitrile. Yield: 4.2 gm of colorless crystals. M.p.: 125°–127° C.

EXAMPLE 7

1-(2-Cyano-6-n-hexanoylaminophenoxy)-3-(2-methyl-butinyl-3-amino-2)-2-propanol hydrochloride Ten grams (0.31 mol) of 1-(2-cyano-6-n-hexanoylaminophenoxy)-3-chloro-2-propanol were dissolved in 80 ml of ethanol and, after addition of 12.6 ml (0.12 mol) of 2-methylbutin-3-amine-2, the mixture was refluxed for 2 hours. After working up according to the procedure described in Example 6, the aqueous acid phase was adjusted alkaline with NaOH, and the precipitating oily base was taken up in ethyl acetate and further processed as described above. The raw base was purified over a silica gel column. The purified preparation was dissolved in acetonitrile, acidified with alcoholic HCl, and brought to crystallization with addition of ether. The hydrochloride was recrystallized once more from acetonitrile with addition of ether. Yield: 2.1 gm. M.p: 133°–134° C.

EXAMPLE 8

1-(2-Cyano-6-n-hetanoylaminophenoxy)-3-(3-ethylpentinyl-4-amino-3)-2-propanol-hydrochloride Sixteen grams (0.047 mol) of 1-(2-cyano-6-n-heptanoylaminophenoxy)-3-chloro-2-propanol were dissolved in 80 ml of ethanol, and, after addition of 26 ml (0.2 mol) of 3-ethylpentin-4-amine-3, the mixture was refluxed for two hours. After working up according to the procedure described in Example 6, the raw base was purified over a silica gel column. After the uniform fractions were united, the base was obtained by distilling off the solvent mixture. The base was then taken up in dilute HCl and extracted with ether. The resulting crystalline product that precipitated was isolated and then recrystallized from acetonitrile. Yield: 2.7 gm. M.p.: 188°–189° C.

EXAMPLE 9

1-(2-Cyano-6-n-pentanoylaminophenoxy)-3-(2-methyl-butin-3-amino-2)-2-propanol hydrochloride Eleven grams (0.036 mol) of 1-(2-cyano-6-n-pentanoyl-aminophenoxy)-3-chloro-2-propanol were refluxed for three hours after dissolution in 80 ml of ethanol and addition of 11.6 ml (0.11 mol) of 2-methylbutin-3-amine-2. Processing and column separation was effected as described in Example 8. The uniform basic residue of the column fractions was dissolved in a small amount of acetonitrile, stirred with etheric HCl, and brought to crystallization with addition of ether. The colorless crystals were recovered by suction filtration and then recrystallized from acetonitrile. Yield: 1.4 gm. M.p.: 144°–145° C.

EXAMPLE 10

1-(Cyano-6-n-pentanoylaminophenoxy)-3-(2-ethylpentin-4-amino-3)-2-propanol hydrochloride Eleven grams (0.036 mol) of 1-(2-cyano-6-n-pentanoylaminophenoxy)-3-chloro-2-propanol were reacted and processed with addition of 14.8 ml (0.11 mol) of 3-ethylpentin-4-amine-3 as described in Example 8. Purification of the raw base was effected as well via a silica gel column. Then the base was dissolved in a small amount of acetonitrile and acidified with etheric HCl. With addition of ether and some petroleum ether, the crystallization of the hydrochloride was initiated. An amount of 2.6 gm of pure substance was recovered. M.p.: 196°–198° C.

EXAMPLE 11

1-(2-Cyano-6-n-hexanoylaminophenoxy)-3-(2-ethylpentin-4-amino-3)-2-propanol hydrochloride Eleven grams (0.033 mol) of 1-(2-cyano-6-n-hexanoylaminophenoxy)-3-chloro-2-propanol were refluxed in 70 ml of ethanol with 12 ml (0.09 mol) of 3-ethyl-pentin-4-amine-3 for 2.5 hours. Processing and purification over a silica gel column was effected as described in Example 8. The amine thus purified was dissolved in ether and stirred with etheric HCl, and the hydrochloride was filled with hexane. The solid substance was recrystallized from acetonitrile. Yield: 2.9 gm. M.p.: 192°–193° C.

The compounds of the present invention, that is, those embraced by formula I above and their non-toxic, pharmacologically acceptable acid addition salts, have useful pharmacodynamic properties.

More particularly, in the animal test on guinea pigs they exhibit $\beta$-adrenolytic properties and may therefore be used, for example, for treatment and prophylaxis of diseases of the coronaries and for treatment of cardiac arrhythmia, in particular of tachycardia. The hypotensive properties of the compounds are of therapeutic interest as well. In comparison to the known $\beta$-receptor blocker, for example, the commercial product of similar structure 1-(2-acetyl-4-butyroylaminophenoxy-2-hydroxy-3-isopropylaminopropane (acebutolol), the compounds have the advantage of a considerably lower toxicity, a better $\beta$-isoprenaline antagonistic activity and an excellent organ selectivity. These parameters were measured by means of the following test models:

1. Inhibition of the isoprenaline tachycardia (isorenaline antagonistic activity)

Method: Inhibition of the tachycardiac reaction to a standard dose of isoprenaline and effect upon the basal heart rate of increasing i.v. dosages of a $\beta$-adrenolytic.

Animal material: Guinea pigs of both sexes with body weights of 270–350 gm, group keeping, standard feed and water until beginning of test ad libitum. Sixteen hours before beginning of test withdrawal of nutrition.

Anesthesia: Ethylurethane 1.75 gm/kg as 20% solution intraperitoneally; if required, it was reinjected.

Preparation: Cannulation of a Vena jugularis exterior for intravenous injection: Insertion of a tracheal cannula and artificial respiration; subcutaneous needle electrodes for recording of the ECG, as a rule extremity lead II, recording rate 25 mm/sec; rectal thermometer for control of body temperature which is kept constant at 34°–36° C. by means of an infrared heat lamp controlled by an automatic electronic heat sensing device.

Test Procedure: The heart rate is determined by counting the r-waves in the ECG, each from a recording time of 3–4 seconds. About 30 minutes after the preparation the normal heart rate is recorded an averaged five times in intervals of 2 minutes. Subsequently, 1 μg/kg of isoprenaline is injected i.v. as adrenergic stimulant, and afterwards the heart rate is recorded repeated for 3 minutes each 30 seconds. The injections of isoprenaline are repeated during the whole time of the test at intervals of 30 minutes. If the spontaneous rate remains almost constant and if the tachycardiac reaction upon the first 2–3 isoprenaline administrations is homogeneous, then there is injected i.v.—15 minutes after the last and 15 minutes before the next isoprenaline reaction—the first dose of the test compound. Further doses of the test compound increasing in geometric series follow at intervals of 60 minutes until a distinct inhibition of the isoprenaline tachycardia has been reached.

2. Test for cardioselectivity on the conscious guinea pig

Principle: According to the method of D. Dunlop and R. G. Shanks [Brit. J. Pharmacol. 32, 201 (1968)] conscious guinea pigs are exposed to a lethal dose of a histamine aerosol. By pre-treatment with isoprenaline the animals are protected from the lethal effect of the histamine. A β-adrenolytic neutralizes the isoprenaline, so that the protection against histamine bronchospasms is lost if a non-cardioselective substance is involved. If a cardiac-active β-adrenolytic substance does not show any antagonism against isoprenaline in this test, the presence of cardioselectivity (for so-called $\beta_1$-receptors) may be assumed.

Animal material: Guinea pigs of both sexes (6 animals per dose), with 350–400 gm body weight, group keeping. Standard feed and water until beginning of test ad libitum. Sixteen hours before beginning of test withdrawal of feed.

Test procedure: Groups of 6 animals each (3 male and 3 female) are treated subcuteneously with 5 or more different doses of the β-adrenolytic. Fifteen minutes later they get a contralateral subcutaneous injection of 0.01 mg/kg isoprenaline. After another 15 minutes have passed the animals are placed into a cylindrical chamber of 2 liters capacity, exposed for 45 seconds to an aqueous histamine aerosol (1.25%), and subsequently the mortality is evaluated.

Evaluation: The mortality is plotted against the logarithm of the dose, and the $LD_{50}$ is determined according to J. LITCHFIELD and F. WILCOXON (J. Pharmacol. exp. Therap. 96, 99–113, 1949). With the $LD_{50}$ from this test and the cardiac $ED_{50}$ from the isoprenaline tachycardia inhibition test (anesthetized guinea pigs) a selectivity quotient ($LD_{50}/ED_{50}$) is formed. A substance is considered to be cardioselective if the quotient is larger than 1.

Particularly effective are those compounds of the formula I in which $R_3$ and $R_4$ are methyl, i.e., substituted p-acylamino-1-phenoxy-3-(2-methyl-butinyl-3-amino-2)-2-propanols. Especially effective is 1-(2-cyano-4-n-hexanoylamino)-phenoxy-3-(2-methylbutinyl-3-amino-2)-2-propanol or its salts. In comparison to acebutolol this compound exhibits an about 20 times stronger isoprenaline-antagonistic activity.

For pharmaceutical purposes the compounds of the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups and the like. One effective oral dosage unit of the compounds according to the present invention is from 0.013 to 4.0 mgm/kg body weight, preferably 0.06 to 1.33 mgm/kg body weight. The parenteral dosage unit range is 0.013 to 0.26 mgm/kg.

The following examples illustrate a few pharmaceutical dosage unit compositions comprising a compound of the present invention as an active ingredient and represent the best modes contemplated of using the invention.

EXAMPLE 12

Tablets

| Component | Amount |
|---|---|
| 1-(2-Cyano-4-n-hexanoylamino-phenoxy)-3-(2-methylbutinyl-3-amino-2)-2-propanol | 40.0 mgm |
| Corn starch | 164.0 mgm |
| Sec. calcium phosphate | 240.0 mgm |
| Magnesium stearate | 1.0 mgm |
| | 445.0 mgm |

Production:

The individual components are admixed thoroughly, and the mixture is granulated in the conventional way. The granulate is compressed into 445 mgm tablets, each containing 40 mgm of the active ingredient.

EXAMPLE 13

Gelatine capsules

The contents of the capsules are compounded from the following ingredients:

| Component | Amount |
|---|---|
| 1-(2-Cyano-4-n-hexanoylamino-phenoxy)-3-(2-methylbutinyl-3-amino-2)-2-propanol | 25.0 mgm |
| Corn starch | 175.0 mgm |
| | 200.0 mgm |

Production:

The ingredients are admixed thoroughly, and 200 mgm portions of the mixture are filled into gelatin capsules of suitable size. Each capsule contains 25 mgm of the active substance.

EXAMPLE 14

Injection solution

The solution is compounded from the following ingredients:

| Component | Amount |
| --- | --- |
| 1-(2-Cyano-4-n-octanoylamino-phenoxy)-3-(2-methylbutinyl-3-amino-2)-2-propanol | 2.5 parts |
| Sodium salt of EDTA (ethylene diamine tetraacetic acid) | 0.2 parts |
| Distilled water q.s. ad | 100.0 parts |

Production:

The active ingredient and the EDTA salt are dissolved in sufficient water, and the solution is diluted with water to the desired volume. The solution is filtered until free from suspended particles and filled into 1 ccm ampules under aseptic conditions. Finally, the ampules are sterilized and sealed. Each ampule contains 25 mgm of the active ingredient.

EXAMPLE 15

Coated sustained release tablets

| Component | Core: Amount |
| --- | --- |
| (−)-1-(2-Cyano-4-n-hexanoyl-phenoxy)-3-(2-methylbutinyl-3-amino-2)-2-propanol | 25.0 gm |
| Carboxymethylcellulose (CMC) | 295.0 gm |
| Stearic acid | 20.0 gm |
| Cellulose acetate phthalate (CAP) | 40.0 gm |
| | 380.0 gm |

Production:

The active ingredient, the CMC and stearic acid are thoroughly admixed, and the mixture is granulated in the conventional way, using a solution of the CAP in 200 ml of a mixture of ethanol and ethyl acetate. Then the granulate is compressed into 380 mgm cores, which are subsequently coated in the conventional way with a sugar-containing 5% solution of polyvinyl pyrrolidone in water. Each coated tablet contains 25 mgm of the active ingredient.

EXAMPLE 16

Tablets

| Component | Amount |
| --- | --- |
| 1-(2-Cyano-4-n-heptanoylamino-phenoxy)-3-(3-ethylpentinyl-4-amino-3)-2-propanol | 35.0 gm |
| 2,6-Bis-(diethanolamino)-4,8-dipiperidino-pyrimido-[5,4-d]-pyrimidine | 75.0 gm |
| Lactose | 164.0 gm |
| Corn starch | 194.0 gm |
| Colloidal silicic acid | 14.0 gm |

-continued

| Component | Amount |
| --- | --- |
| Polyvinyl pyrrolidone | 6.0 gm |
| Magnesium stearate | 2.0 gm |
| Soluble starch | 10.0 gm |
| Total | 500.0 gm |

Production:

The active ingredient is granulated as usual together with lactose, corn starch, colloidal silicic acid and polyvinyl pyrrolidone after admixing same thoroughly using an aqueous solution of the soluble starch. The granulate is admixed with the magnesium stearate and compressed into 500 mgm tablets, each of which contains 35 mgm of the first and 75 mgm of the second active ingredient.

Any one of the other compounds embraced by formula I or a non-toxic, pharmacologically acceptable acid addition salt thereof may be substituted for the particular active ingredient in Examples 12 through 16. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apprent to those skilled in the art that the invention is not limited to these particular embodiments, and that various changes and modifications may be made without departing from the spirit of the invention or the scope of the appended claims.

We claim:

1. A compound of the formula

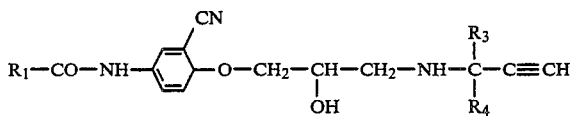

wherein
$R_1$ is a linear or branched alkyl of 4 to 20 carbon atoms;
$R_3$ is hydrogen or alkyl of 1 to 3 carbon atoms; and
$R_4$ is alkyl of 1 to 3 carbon atoms, or $R_3$ and $R_4$, together with each other, are $-(CH_2)_p-$, where p is an integer from 4 to 6, inclusive, or a non-toxic, pharmacologically acceptable acid addition salt thereof.

2. A compound of the formula

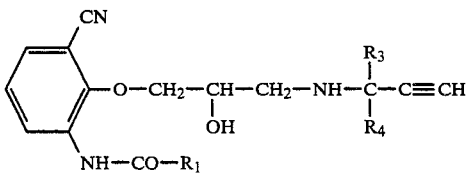

wherein
$R_1$ is a linear or branched alkyl of 4 to 20 carbon atoms;
$R_3$ is hydrogen or alkyl of 1 to 3 carbon atoms; and $R_4$ is alkyl of 1 to 3 carbon atoms, or $R_3$ and $R_4$, together with each other, are $-(CH_2)_p-$, where p is an integer from 4 to 6, inclusive, or a non-toxic, pharmacologically acceptable acid addition salt thereof.

3. A compound of claim 2, where $R_3$ and $R_4$ are both methyl.

4. A β-adrenolytic pharmaceutical dosage unit composition consisting essentially of an inert pharmaceutical carrier and an effective β-adrenolytic amount of a compound of claim 2.

5. A method for the treatment of cardiac arrhythmia which comprises administering to a warm-blooded animal or human an effective amount of a compound of claim 2.

6. The method of claim 5 for the treatment of tachycardia.

7. A method for the treatment or prophylaxis of diseases of the coronaries which comprises administering to a warm-blooded animal or human in need of such treatment an effective amount of a compound of claim 2.

8. A method for the treatment of hypertension which comprises administering to a warm-blooded animal or human an effective amount of a compound of claim 2.

9. A compound of claim 1, where $R_3$ and $R_4$ are both methyl.

10. A compound of claim 1, which is 1-(2-cyano-4-n-hexanoyl-phenoxy)-3-(2-methyl-butinyl-3-amino)-2-propanol or a non-toxic, pharmacologically acceptable acid addition salt thereof.

11. A β-adrenolytic pharmaceutical dosage unit composition consisting essentially of an inert pharmaceutical carrier and an effective β-adrenolytic amount of a compound of claim 1.

12. A method for the treatment of cardiac arrhythmia which comprises administering to a warm-blooded animal or human an effective amount of a compound of claim 1.

13. The method of claim 12 for the treatment of tachycardia.

14. A β-adrenolytic pharmaceutical dosage unit composition consisting essentially of an inert pharmaceutical carrier and an effective β-adrenolytic amount of a compound of claim 10.

15. A method for the treatment of cardiac arrhythmia which comprises administering to a warm-blooded animal or human an effective amount of a compound of claim 10.

16. The method of claim 15 for the treatment of tachycardia.

17. A compound of claim 1 which is 1-(2-cyano-4-n-octanoylamino-phenoxy)-3-(2-methyl-butynyl-3-amino-2)-propanol.

18. A β-adrenolytic pharmaceutical dosage unit composition consisting essentially of an inert pharmaceutical carrier and an effective β-adrenolytic amount of the compound of claim 17.

19. A method for the treatment of cardiac arrhythmia which comprises administering to a warm-blooded animal or human an effective amount of a compound of claim 17.

20. The method of claim 19 for the treatment of tachycardia.

21. A method for the treatment or prophylaxis of diseases of the coronaries which comprises administering to a warm-blooded animal or human in need of such treatment an effective amount of a compound of claim 1.

22. A method for the treatment of hypertension which comprises administering to a warm-blooded animal or human an effective amount of a compound of claim 1.

23. A method for the treatment or prophylaxis of diseases of the coronaries which comprises administering to a warm-blooded animal or human in need of such treatment an effective amount of a compound of claim 10.

24. A method for the treatment of hypertension which comprises administering to a warm-blooded animal or human an effective amount of a compound of claim 10.

25. A method for the treatment or prophylaxis of diseases of the coronaries which comprises administering to a warm-blooded animal or human in need of such treatment an effective amount of a compound of claim 17.

26. A method for the treatment of hypertension which comprises administering to a warm-blooded animal or human an effective amount of a compound of claim 17.

* * * * *

UNITED STATES PATENT AND TRADEMARK OFFICE
CERTIFICATE OF CORRECTION

PATENT NO. : 4,609,672

DATED : September 2, 1986

INVENTOR(S) : HERBERT KOPPE et al.

It is certified that error appears in the above-identified patent and that said Letters Patent is hereby corrected as shown below:

Column 3, line 1, "comounds" should read --compounds--.

Column 3, line 3, "literate" should read -- literature --.

Column 5, line 22, "(0.31" should read -- (0.031 --.

Column 6, line 9, the moiety "1-(Cyano-" should read -- 1-(2-Cyano- --.

Signed and Sealed this

Fourth Day of November, 1986

[SEAL]

*Attest:*

*Attesting Officer*

DONALD J. QUIGG

*Commissioner of Patents and Trademarks*